United States Patent
LaBelle et al.

(10) Patent No.: US 10,386,321 B2
(45) Date of Patent: Aug. 20, 2019

(54) NONINVASIVE BODY FLUID STRESS SENSING

(71) Applicant: Arizona Board of Regents on behalf of Arizona State University, Scottsdale, AZ (US)

(72) Inventors: Jeffrey LaBelle, Tempe, AZ (US); Tina Hakimi, Phoenix, AZ (US); Brittney Cardinell, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/503,364

(22) PCT Filed: Jul. 27, 2015

(86) PCT No.: PCT/US2015/042247
§ 371 (c)(1),
(2) Date: Feb. 10, 2017

(87) PCT Pub. No.: WO2016/025153
PCT Pub. Date: Feb. 18, 2016

(65) Prior Publication Data
US 2017/0234894 A1 Aug. 17, 2017

Related U.S. Application Data

(60) Provisional application No. 62/037,006, filed on Aug. 13, 2014, provisional application No. 62/101,143, filed on Jan. 8, 2015.

(51) Int. Cl.
*G01N 27/327* (2006.01)
*G01N 33/543* (2006.01)
(Continued)

(52) U.S. Cl.
CPC ....... *G01N 27/327* (2013.01); *A61B 5/14507* (2013.01); *A61B 5/14546* (2013.01);
(Continued)

(58) Field of Classification Search
CPC ............. G01N 27/327; G01N 33/5436; G01N 33/743; G01N 27/3273; G01N 27/301;
(Continued)

(56) References Cited

U.S. PATENT DOCUMENTS 5,066,372 A * 11/1991 Weetall .............. G01N 27/3271
204/403.11
5,234,566 A 8/1993 Osman et al.
(Continued)

FOREIGN PATENT DOCUMENTS

WO 2012009322 A1 1/2012
WO 2016025153 A1 2/2016

OTHER PUBLICATIONS

AD Instruments, "HRV", AD Instruments, obtained from archive. org capture of Jan. 10, 2010, <https://web.archive.org/web/20100110063726/http://www.adinstruments.com:80/solutions/research/HRV>, accessed on Mar. 22, 2018.
(Continued)

*Primary Examiner* — Melanie Brown
(74) *Attorney, Agent, or Firm* — Gavin J. Milczarek-Desai; Quarles & Brady LLP

(57) ABSTRACT

Electrochemical impedance-based label-free and rapid biosensor for select bodily fluid biomolecule levels. Monoclonal antibodies to of biomolecule such as Cortisol were covalently attached to a 16-mercaptohexadecanoic acid functionalized gold working electrode using zero-length crosslinkers N-(3-dimethylaminopropyl)-N-ethylcarbodiimide and 10 mM N-hydroxysulfosuccinimide. Cortisol was detected in phosphate buffered saline (simulated tear fluid)
(Continued)

using a simple ferrocyanide reagent with a lower limit of detection of 18.73 pM and less than 10% relative standard deviation.

8 Claims, 17 Drawing Sheets

(51) Int. Cl.
*A61B 5/145* (2006.01)
*G01N 27/02* (2006.01)
*G01N 27/30* (2006.01)
*G01N 33/74* (2006.01)
*A61B 5/053* (2006.01)
*A61B 5/16* (2006.01)

(52) U.S. Cl.
CPC ......... *G01N 27/026* (2013.01); *G01N 27/301* (2013.01); *G01N 27/3273* (2013.01); *G01N 33/5436* (2013.01); *G01N 33/5438* (2013.01); *G01N 33/743* (2013.01); *A61B 5/053* (2013.01); *A61B 5/165* (2013.01); *A61B 2562/0215* (2017.08); *G01N 2800/7004* (2013.01)

(58) Field of Classification Search
CPC .............. G01N 27/026; G01N 33/5438; A61B 5/14546; A61B 5/14507; A61B 5/165; A61B 5/053
See application file for complete search history.

(56) References Cited

U.S. PATENT DOCUMENTS

| | | |
|---|---|---|
| 7,112,328 B2 | 9/2006 | Marinkovich |
| 7,112,816 B2 | 9/2006 | Schlaf et al. |
| 8,778,269 B2 | 7/2014 | Joshi et al. |
| 2002/0137032 A1 | 9/2002 | Hefti |
| 2005/0003560 A1 | 1/2005 | Zeng et al. |
| 2008/0124776 A1 | 5/2008 | Wei |
| 2008/0185295 A1 | 8/2008 | Briman et al. |
| 2009/0082691 A1 | 3/2009 | Denison et al. |
| 2009/0092965 A1 | 4/2009 | Weiss et al. |
| 2009/0117571 A1 | 5/2009 | Solanki et al. |
| 2009/0117589 A1 | 5/2009 | Southern |
| 2010/0203391 A1* | 8/2010 | Lopatin .................. B82Y 30/00 429/231.8 |
| 2011/0100812 A1* | 5/2011 | Takenaka ............. G01N 27/403 204/412 |
| 2013/0183243 A1* | 7/2013 | LaBelle ............. G01N 33/5438 424/9.1 |
| 2013/0213823 A1* | 8/2013 | Arumugam ........ G01N 27/3278 205/794.5 |
| 2013/0316430 A1* | 11/2013 | Pundir .................... C12N 11/18 435/175 |
| 2013/0332085 A1 | 12/2013 | Yang et al. |
| 2015/0338367 A1* | 11/2015 | Hu ....................... G01N 27/333 205/780 |

OTHER PUBLICATIONS

Adamson, T. et al., "Detection of 1,5-Anhydroglucitol by Electrochemical Impedance Spectroscopy", Journal of Diabetes Science and Technology, Mar. 2014 (available online Feb. 2014), 8(2), pp. 350-355.
Adamson, T. et al., "The promise of electrochemical impedance spectroscopy as novel technology for the management of patients with diabetes mellitus", Analyst, Sep. 2012 (available online Jul. 2012), 137(18), pp. 4179-4187.
Arya, S. et al., "Polyaniline protected gold nanoparticles based mediator and label free electrochemical cortisol biosensor", Biosensors and Bioelectronics, Oct. 2011 (available online Jul. 2011), 28(1), pp. 166-173.
Banbury, L., "Stress Biomarkers in the Tear Film", PhD thesis, Southern Cross University, Lismore, NSW, p. 65., Oct. 2009.
Bishop, D. et al., "A Disposable Tear Glucose Biosensor—Part 1: Design and Concept Testing", Journal of Diabetes Science and Technology, Mar. 2010, 4(2), pp. 299-306.
Bryan, T. et al., "An optimised electrochemical biosensor for the label-free detection of C-reactive protein in blood", Biosensors and Bioelectronics, Jan. 2013 (available online Jul. 2012), 39(1), pp. 94-98.
Chen, S.-Y. et al., "Association of heart rate variability with clinical outcome in Parkinsonian patients after subthalamic deep brain stimulation: A retrospective cohort study", Sep. 2011 (available online Aug. 2011), 110(9), pp. 593-599.
Chrousus, G., "Stress and disorders of the stress system", Nature Reviews Endocrinology, Jul. 2009 (available online Jun. 2009), 5(7), pp. 374-381.
Cook, E. et al., "Simultaneous measurement of six cytokines in a single sample of human tears using microparticle-based flow cytometry: allergics vs. non-allergics", Journal of Immunological Methods, Aug. 2001 (available online Jun. 2001), 254(1-2), pp. 109-118.
Dai, M. et al., Mesoporous carbon amperometric glucose sensors using inexpensive, commercial methacrylate-based binders, Analytica Chimica Acta, Aug. 2012 (available online Jun. 2012), vol. 738, pp. 27-34.
Dai, M. et al., "Ordered Mesoporous Carbon Composite Films Containing Cobalt Oxide and Vanadia for Electrochemical Applications", May 2011, 23(11), pp. 2869-2878.
Fullard, R. et al., "Protein levels in nonstimulated and stimulated tears of normal human subjects", Investigative Ophthalmology & Visual Science, Jun. 1990, 31(6), pp. 1119-1126.
Ganzel, B. et al., "Allostasis and the human brain: Integrating models of stress from the social and life sciences", Psychological Review, Jan. 2010, 117(1), pp. 134-174.
Garcher, C. et al., "CA 19-9 ELISA test: a new method for studying mucus changes in tears", British Journal of Ophthalmology, Jan. 1998, 82(1), pp. 88-90.
Giannopoulou, C. et al., "Effect of inflammation, smoking and stress on gingival crevicular fluid cytokine level", Journal of Clinical Periodontology, Mar. 2003, 30(2), pp. 145-153.
Gonzalez, S. et al., "The Development of an At-Risk Biosensor for Cardiovascular Disease", Biosensors Journal, 2012, vol. 1, article ID 235493, 5 pages.
Huang, C. et al., "Psychological stress during exercise: Immunoendocrine and oxidative responses", Experimental Biology and Medicine, Dec. 2010, 235(12), pp. 1498-1504.
La Belle, J. et al., "A cytokine immunosensor for multiple sclerosis detection based upon label-free electrochemical impedance spectroscopy", Biosensors and Bioelectronics, Oct. 2007 (available online Jul. 2007), 23(3), pp. 428-431.
La Belle, J. et al., "A disposable tear glucose biosensor—part 2: system integration and model validation", Journal of Diabetes Science and Technology, Mar. 2010, 4(2), pp. 307-311.
La Belle, J. et al., "Development of a novel single sensor multiplexed marker assay", Analyst, Apr. 2011 (available online Feb. 2011), 136(7), pp. 1496-1501.
Lan, K. et al., "A Disposable Tear Glucose Biosensor—Part 3: Assessment of Enzymatic Specificity", Journal of Diabetes Science and Technology, Sep. 2011, 5(5), pp. 1108-1115.
Lehrer, J., "Under Pressure: The Search for a Stress Vaccine", Wired Magazine, Jul. 2010, originally retrieved May 3, 2011, obtained from archive.org capture of Jan. 15, 2015, <https://web.archive.org/web/20150115095016/http://www.wired.com:80/2010/07/ff_stress_cure/all>, accessed on Mar. 22, 2018.
Martin, X. et al., "Dopamine and its metabolites in human tears", European Journal of Ophthalmology, Apr. 1993, 3(2), pp. 83-88.
McMurray, D. et al., "Effect of moderate malnutrition on concentrations of immunoglobulins and enzymes in tears and saliva of young Colombian children", American Journal of Clinical Nutrition, Dec. 1977, 30(12), pp. 1944-1948.
Molloy, M. et al., "Establishment of the human reflex tear two-dimensional polyacrylamide gel electrophoresis reference map: New proteins of potential diagnostic value", Electrophoresis, 1997, 18(15), pp. 2811-2815.

(56) References Cited

OTHER PUBLICATIONS

Moschos, M. et al., "Quantitative determination of glycosaminoglycans in tears of diabetic patients", Clinical Ophthalmology, Sep. 2008, 2(3), pp. 581-584.

Nandakumar, V. et al., "A Low-Cost Electrochemical Biosensor for Rapid Bacterial Detection", IEEE Sensors Journal, Jan. 2011 (available Sep. 2010), 11(1), pp. 210-216.

Office Action for U.S. Appl. No. 13/809,387, dated Feb. 1, 2017.

Office Action for U.S. Appl. No. 13/809,387, dated Sep. 26, 2016.

Patent Cooperation Treaty, International Bureau, International Preliminary Report on Patentability for PCT/US2011/043652, 8 pages, dated Jan. 15, 2013.

Patent Cooperation Treaty, International Bureau, International Preliminary Report on Patentability for PCT/US2015/042247, 6 pages, dated Feb. 14, 2017.

Patent Cooperation Treaty, International Searching Authority, International Search Report for PCT/US2011/043652, 2 pages, dated Oct. 31, 2011.

Patent Cooperation Treaty, International Searching Authority, International Search Report for PCT/US2015/042247, 2 pages, dated Oct. 28, 2015.

Patent Cooperation Treaty, International Searching Authority, Written Opinion for PCT/US2011/043652, 7 pages, dated Oct. 31, 2011.

Patent Cooperation Treaty, International Searching Authority, Written Opinion for PCT/US2015/042247, 5 pages, dated Oct. 28, 2015.

Romero, L. et al., "The Reactive Scope Model—a new model integrating homeostasis, allostasis, and stress", Hormones and Behavior, Mar. 2009 (available online Jan. 2009), 55(3), pp. 375-389.

Segerstorm, S., "Resources, Stress, and Immunity: An Ecological Perspective on Human Psychoneuroimmunology", Annals of Behavioral Medicine, Jun. 2010, 40(1), pp. 114-125.

Smolander, J. et al., "Estimating oxygen consumption from heart rate and heart rate variability without individual calibration", Clinical Physiology and Functional Imaging, Jul. 2011 (available online Feb. 2011), 31(4), pp. 266-271.

Song, J. et al., "Myocardial ischemia analysis based on electrocardiogram QRS complex", Australasian Physical & Engineering Sciences in Medicine, Dec. 2011 (available online Oct. 2011), 34(4), pp. 515-521.

Ubels, J. et al., "Vitamin A is present as retinol in the tears of humans and rabbits", Current Eye Research, Jun. 1984, 3(6), pp. 815-822.

Van Haeringen, N. et al., "Clinical biochemistry of tears", Survey of Ophthalmology, Sep.-Oct. 1981, 26(2), pp. 84-96.

Zubareva, T. et al. ,"Catecholamine content of the lacrimal fluid of healthy people and glaucoma patients", Ophthalmologica, 1977, 175(6), pp. 339-344.

\* cited by examiner

FIG. 1A-B

| Biomarkers | Molecular Recognition Element | Concentration Range of Interest | Optimal Binding Freq | Slope | R^2 | LLD |
|---|---|---|---|---|---|---|
| Cortisol | Anti-cortisol MAB | 0-500 pg/mL | 1.184 Hz | 31.67 | 0.95 | 6.79 pg/mL |
| Dopamine | Anti-dopamine MAB | 0-500 pg/mL | 3125 Hz | 1.79 | 0.986 | 272.56 pg/mL |
| Epinephrine | Anti-epinephrine MAB | 0-500 pg/mL | 4590 Hz | 1.37 | 0.956 | 103.1 pg/mL |
| Glial Fibrillary acidic protein | Anti-GFAP MAB | 0-2800 pg/mL | 17.44 Hz | 132.9 | 0.9527 | 106.95 pg/mL |
| Glucose | glucose oxidase; glucose dehydrogenase | 0-700 mg/dL | 1170 Hz | 3.53 | 0.9 | 38 mg/dL |
| Neuron specific enolase | Anti-NSE MAB | 0-30,000 pg/mL | 459 Hz | 7.55 | 0.98 | 3.30 pg/mL |
| Norepinephrine | phenylethanolamine N-methyltransferase | 0-500 pg/mL | 371.1 Hz | 20.899 | 0.963 | 94.18 pg/mL |
| S-100B | Anti-S-100B MAB | 0-30,000 pg/mL | 1758 Hz | 3.056 | 0.96 | 84.06 pg/mL |
| TNF-alpha | Anti-TNF-alpha MAB | 0-75 pg/mL | 57.44 Hz | 39.878 | 0.9208 | 116.96 pg/mL |
| Lactate | lactate oxidase | in progress | in progress | in progress | in progress | in progress |

FIG. 7

NONINVASIVE BODY FLUID STRESS SENSING

CROSS-REFERENCE TO RELATED APPLICATIONS

This application is a 371 application of PCT/US2015/042247 filed Jul. 27, 2015, which claims the benefit of U.S. Provisional Patent Application No. 62/037,006, filed Aug. 13, 2014, and U.S. Provisional Patent Application No. 62/101,143, filed Jan. 8, 2015, which are incorporated herein by reference as if set forth in their entirety.

TECHNICAL FIELD

This disclosure relates to the field electrochemical sensing.

BACKGROUND

Over the past 40 years, chronic stress has been increasingly implicated in a wide and growing variety of humanity's most lethal and life-altering diseases. These include such severe conditions as diabetes, Alzheimer's disease, heart attacks, depression, osteoporosis, and immunosuppression, as well as nonlethal but still unfortunate problems like common colds, back pain, and even erectile dysfunction. In fact, scientific literature shows that stress affects life expectancy in developed countries more than genetics and behavioral factors such as smoking.

Given the enormous impact of stress on human life and health worldwide, there is great potential in measuring and treating stress on a population-wide scale. Although stress is often described as a subjective emotional state, medically it has important biochemical and physiological effects. These effects that can be quantified, such as increased levels of a group of certain hormones including the glucocorticoids and catecholamines. However, physiological concentrations of these hormones, even when elevated, are often extremely low in tears, saliva and serum ($38.9 \pm 15.5$, $46.3 \pm 16.0$, and $489.7 \pm 177.4$ nM respectively), making precise measurement a continuing technical challenge.

SUMMARY

A modified electrochemical sensor using a microfluidic tear fluid capture system has been made to detect stress and/or trauma related biomolecules, such as cortisol. Moreover, other bodily fluids such as saliva or blood may be utilized.

In one embodiment, monoclonal antibodies were covalently attached to a 16-mercaptohexadecanoic acid functionalized gold working electrode using zero-length crosslinkers N-(3-dimethylaminopropyi}-N-ethylcarbodiimide and 1 OmM N-hydroxysulfosuccinimide. Cortisol was detected in phosphate buffered saline (simulated tear fluid) using a simple ferrocyanide reagent with a lower limit of detection of 18.73 pM and less than 10% relative standard deviation. The cortisol assay presented herein retains a highly reproducible and ultralow level of detection in a label-free and rapid response configuration with more than adequate sensitivity for tear cortisol measurement.

These and other aspects of the embodiments disclosed herein will be apparent upon reference to the following detailed description and figures.

DESCRIPTION OF DRAWINGS

FIG. 7 depicts a summary of biomarker data.

DETAILED DESCRIPTION

Though blood has historically been the standard diagnostic testing fluid, tear fluid has gained attention as a powerful sensing medium in recent years for three major reasons. Firstly, the tear film contains a vast number of biomarkers.

Secondly, the relative ease in acquiring tear fluid compared to acquiring blood from the patient has made the tears an ideal substitute for the blood in diagnostic testing. Finally, tear fluid, like saliva, is much less complex in composition than blood and contains fewer proteins which might interfere with electrochemical sensing.

Though there are some drawbacks to using tears (for example the available volume and target concentration are much less than those of blood), these difficulties are outweighed by the benefits of easier and less invasive sampling and better sensor performance with less background interference from non-target substances, proving the tear film to be the ideal diagnostic fluid for the stress sensor while still containing measurable levels of cortisol.

Thus, in one aspect of the disclosure herein, a screen printed electrode, an embodiment of which is shown in FIG. 1A-B, captures a tear sample via a novel microfluidic capture system that brings the sample to the reagents and one or more molecular recognition units for cortisol (or other stress markers found in tears) encapsulated in the mesoporous carbon inks of the sensor themselves has been developed using rapid, label-free and multiplexible electrochemical impedance spectroscopy (MEIS) that can be utilized at the point on care/injury. The molecular recognition units may include one or more of antibodies, aptamers, peptides, synbodies, nucleic acids, tentacle probes, proteins, and the like. Moreover, mesoporous carbon inks have been found to block interferents, leading to better test results.

Although stress is often described as a subjective emotional state, it has been shown to have important biochemical and physiological effects with dramatic impacts on human health. Consequently, monitoring stress levels by sensing biochemical markers has the potential for making a dramatic impact on stress management. Electrochemical impedance spectroscopy (EIS) is one such sensing method that has been successful in label-free detection of a variety of extremely low concentration targets, including whole cell, protein biomarker, and small molecule targets. Compared to other electrochemical methods, EIS has advantages including speed (90 seconds per measurement), simplicity (no labeling requirement as with "sandwich" assays) and sensitivity (detection of picomolar-concentration targets below the detection limits of many other methods). This label-free sensing capability and ultralow detection limits make EIS an ideal sensing mechanism for cortisol in the tears.

EXAMPLE 1

Figure 1:
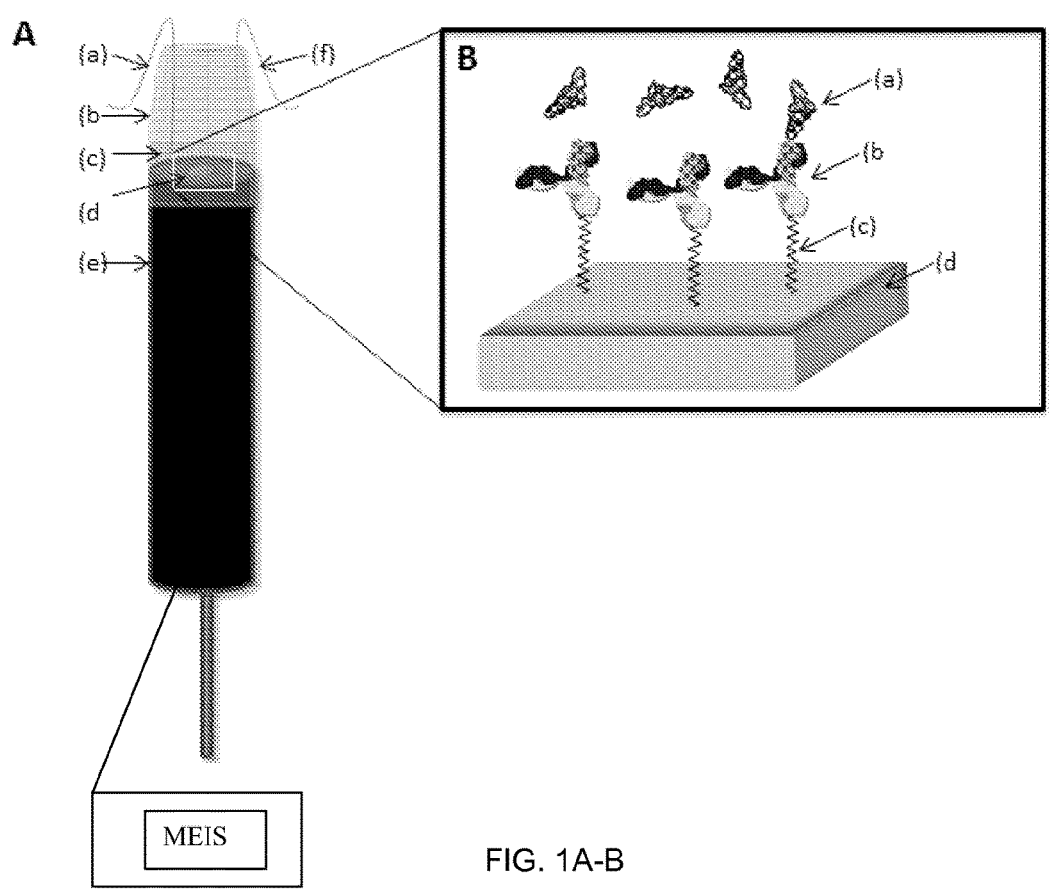
FIG. 1. A. Basic scheme of an embodiment of an apparatus with three-electrode system including (a) Ag/AgCl Reference Electrode, (b) Sensing Well, (c) Sample, (d) Au Working Electrode, (e) GDE, and (f) Pt Counter Electrode. Note that all materials are exemplary and can be substituted for by other suitable materials. Additionally, a multiplexible electrochemical impedance spectroscopy (MEIS) system in operable connection with the apparatus is schematically depicted. B. Sample with target (a) Cortisol is placed within the sensing well on surface of covalently immobilized monoclonal antibody (MAb) on the gold working electrode surface with MAb (b) immobilized to the gold surface (d) covalently with 16-MHDA (c) and EDC/NHS. Cortisol (a) target in sample binds to the MAb.

A standard three-electrode system was used for impedance spectroscopy measurements. The system is comprised of a Ag/AgCl reference electrode (CH Instruments, Austin, Tex.), a gold disk working electrode (GDE) (CH Instruments, Austin, Tex.), and a platinum counter electrode (CH Instruments, Austin, Tex.), with anti-cortisol antibodies (Sigma-Aldrich, St. Louis, Mo.) covalently attached to the working electrode surface to detect cortisol in the sample solution. A 1000 µL pipette tip (VWR International, Radnor, Pa.) was with the tip clipped with a razor and fitted tightly over the GDE to create a plastic "well" able to hold around 0.2 mL of sample liquid. A diagram of this system is shown in FIG. 1.

Phosphate buffered saline (PBS) at pH 7.4 (EMD Biosciences, La Jolla, Calif.) was used to make all solutions unless otherwise noted. In order to immobilize anti-cortisol antibody onto the surface of the gold disk electrode (GDE), the GDE was first wet-polished with 120 figure-eight passes on 3 µm aluminum oxide grit (CH Instruments, Austin, Tex.) and rinsed with distilled water. The 120 figure-eight polishing was then repeated with 1 µm and then 0.05 µm grit (CH Instruments, Austin, Tex.), after which the GDE was sonicated for 20 min in distilled water. Then, 100 µL of a 1 mM 16-mercaptohexadecanoic acid (16-MHDA) (Sigma-Aldrich, St. Louis, Mo.) solution in reagent grade ethanol was placed into the sensing well and sealed in with Parafilm for 1 hr at room temperature. Next, the surface and sides of the GDE and sensing well were carefully rinsed with distilled water. Control EIS measurements were performed on the 16-MHDA-functionalized GDE using a "redox probe" of 100 mM potassium ferrocyanide (Sigma-Aldrich, St. Louis, Mo.) in PBS buffer to ensure an adequate and similar amount of MHDA was immobilized to each GDE. This was determined by analyzing the impedance response of each individual GDE for comparability to one another.

Then, 100 µL of a PBS solution containing 40 mMN-(3-dimethylaminopropyl)-N-ethylcarbodiimide (EDC) (Pierce Biotechnology) and 10 mM N-hydroxysulfosuccinimide (sulfo-NHS) (VWR international) was placed in the sensing well. After 1 hr of incubation at room temperature, the electrode was rinsed with PBS buffer. Next, a 100 µL droplet of a 10 µg/ml solution of anti-cortisol IgG (Aldrich) in PBS buffer was placed on the electrode and left at room temperature for 1 hr, then rinsed off with PBS buffer. Finally, 100 µL of 1 mM ethanolamine (Sigma-Aldrich, St. Louis, Mo.) in distilled water was added to the sensing well and incubated for 30 min at room temperature to block all the unreacted carboxyl groups of the 16-MHDA and EDC/NHS. The electrode was then rinsed carefully with PBS buffer and stored in PBS at 4° C. until use.

Electrochemical impedance measurements were made using a CHI660C Electrochemical Workstation (CH Instruments, Houston, Tex.). Cortisol (Sigma-Aldrich, St. Louis, Mo.) sample concentrations from 0 to 10,000 pg/mL (0 to 27.59 nM) were made in redox probe solution and stored at 4° C. until use. Each concentration of cortisol was then measured on each of the antibody-immobilized electrodes.

For each measurement, 100 µL of the cortisol and redox probe solution was placed in the sensing well of the antibody-immobilized GDE. The AC potential applied to the sample had an amplitude of 5 mV with a formal potential (DC offset) of 150 mV, determined by a CV run on the bare (pre-immobilization) electrodes with redox probe. The AC voltage was applied at a range of frequencies from 1 to 100,000 Hz in 90 sec scan and the impedance magnitude and phase were recorded at each frequency for that sample. Real and imaginary impedances were calculated and plotted in a Nyquist plot for each sample. After each measurement, the GDE and sensing well were rinsed thoroughly with PBS prior to adding the next sample.

For each electrode at each AC frequency tested, the impedance magnitude at each cortisol concentration was correlated to log(concentration) with a slope and $R^2$ calculated. The impedance slopes and $R^2$ values were each plotted against frequency in order to find the frequency which resulted in the best balance of high slope and $R^2$. The impedance values measured at this "optimal" frequency were then used to generate the final concentration gradient allowing cortisol concentration to be estimated from impedance.

Figure 2:
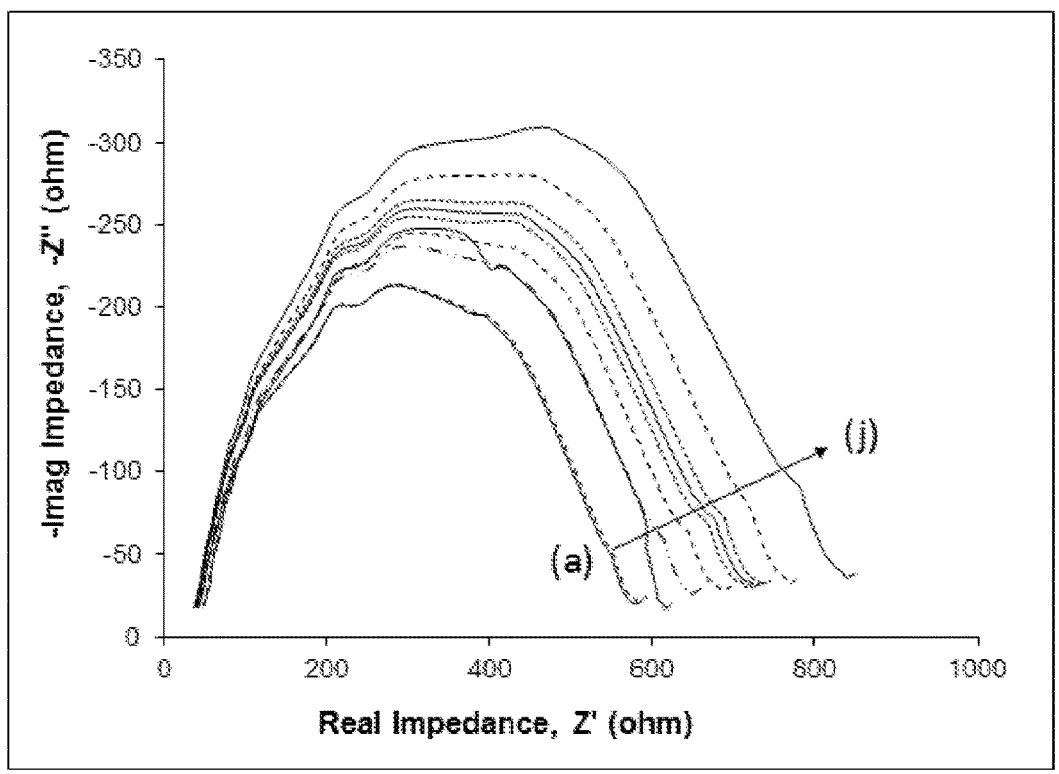
FIG. 2. Nyquist plots of nine different MAb immobilized electrodes run in Cortisol target solutions at: (a) 0 pg/ml, (b) 1 pg/ml, (c) 5 pg/ml, (d) 10 pg/ml, (e) 50 pg/ml, (f) 100 pg/ml, (g) 500 pg/ml, (h) 1000 pg/ml, (i) 5000 pg/ml, and (j) 10000 pg/ml in PBS buffer with 100 mM potassium ferrocyanide redox probe.

AC sweeps of the bare, antibody immobilized, and biomarker (cortisol) bound electrodes yielded Nyquist plots. Nyquist plots of nine different concentrations of cortisol binding to one representative electrode are shown in FIG. 2. As the sample cortisol concentration increases, more cortisol binds to the antibodies on the electrode surface, thus increasing the magnitude of the impedance at all frequencies and pushing the Nyquist plots further out from the origin.

As expected, when the concentration of biomarker in vitro and therefore bound to the antibody increased, the impedance measured by the system (and therefore the signal) increased as well.

Figure 3A:
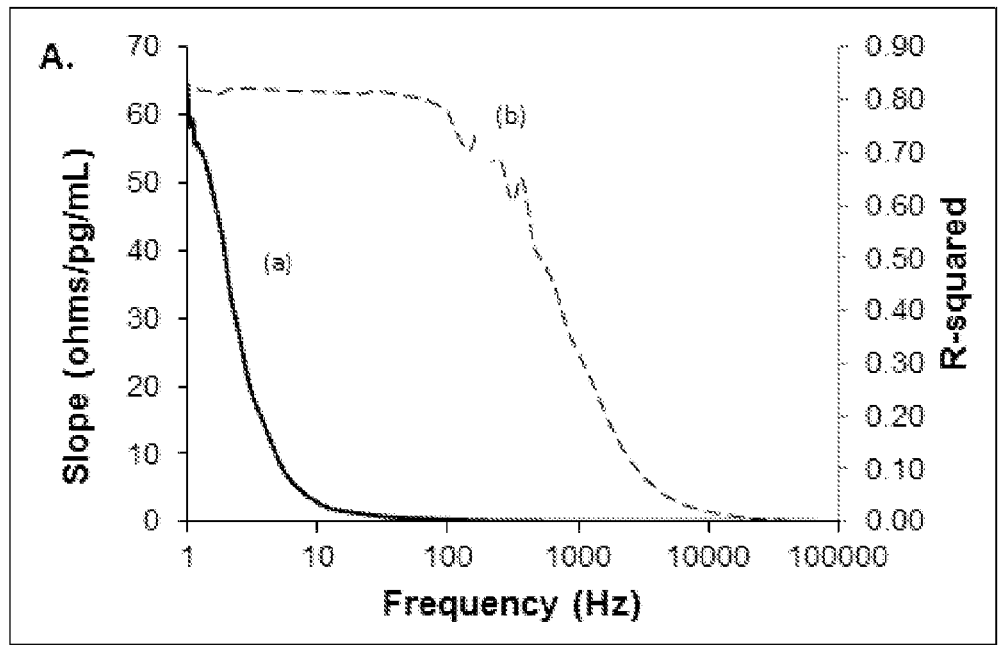
FIG. 3A depicts from the concentration gradient the calculations of (a) slope and (b) R-square (tightness of fit) that are made and plotted again frequency to determine optimal frequency of detection.

The slope and $R^2$ of a correlation plot of impedance versus target concentration change as a function of the AC potential frequency. One representative electrode is shown in FIG. 3a. Larger slope is desirable as it corresponds to a larger signal size (greater difference in impedance values between different cortisol concentrations) which is easier to measure with low proportional error. Larger $R^2$ is desirable as it indicates increased accuracy in the estimate of cortisol concentration provided by the measurement. In FIG. 3a it can be seen that $R^2$ is quite high for a range of frequencies below 100 Hz, but slope is by far the best (largest) at very low frequencies and drops off rapidly as the frequency is increased. For all electrodes tested, the optimal frequency to maximize slope was found to be 1.18 Hz. This is, therefore, the estimated optimal frequency at which the cortisol-antibody interaction is most effectively detected by EIS.

Figure 3B:
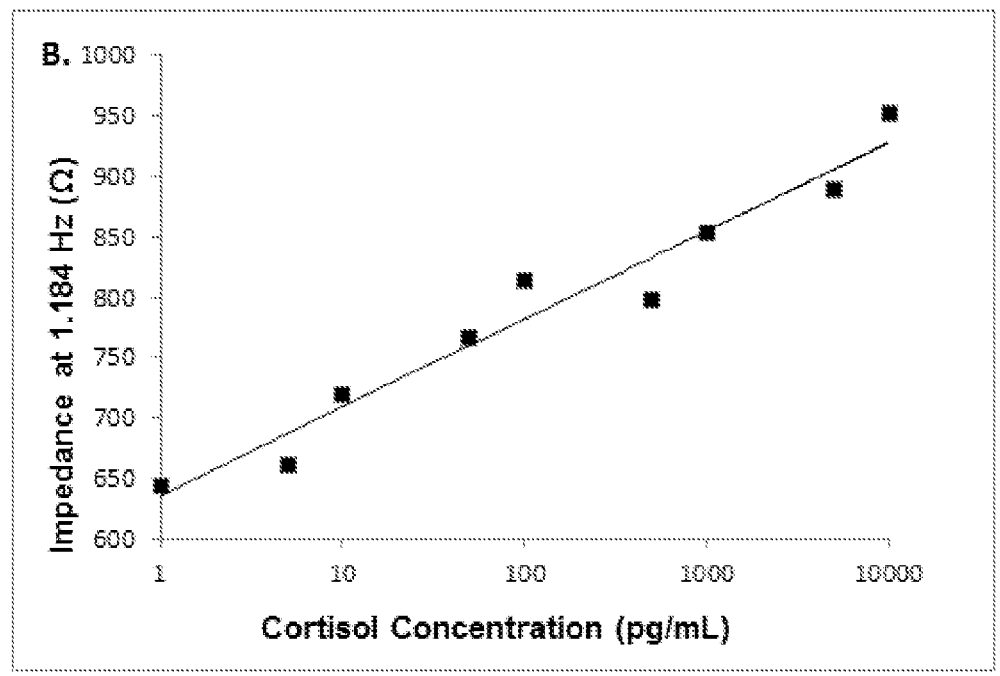
FIG. 3B. Impedance at 1.184 Hz was used and plotted against concentration of Cortisol in PBS over physiological ranges and beyond showing sensor dynamic range (n=3). A slope of 31.672 ohms/pg/mL is observed with an $R^2$ of 0.9532 and 10% RSD at the highest concentration variance.

At this frequency (1.18 Hz), impedance data was compiled for several sensors and plotted against corresponding concentrations to create the impedance gradient shown in FIG. 3b. This gradient shows the impeccable accuracy of this method in detecting the extremely low concentrations of cortisol in the tear fluid. From the standard analytical definition of lower limits of detection (LLD), namely 3.3*slope divided by the standard deviation, a LLD of 6.79 pg/mL (18.73 pM) was quantified in under 90 sec detection time per sample. This clearly identifies measured tear cortisol levels with a high degree of accuracy and a <10% sensor to sensor variance at any concentration.

The LLD of 18.73 pM is three full orders of magnitude below the typical cortisol concentration range of around 40 nM in tears, which at first glance seems to be a wildly excessive level of sensitivity for the tear sensing application. But in fact, this ultra-sensitive detection is precisely what is needed to make this cortisol assay translatable from the laboratory to a physical real-world sensor device. A reproducible and reliable sensor requires a low variance in not only the electrochemical assay but also the physical device implementation. Tear sample sizes are unlikely to exceed 10 microliters in volume, as there is just not that much tear liquid to collect, and some of the volume will inevitably be lost by sticking to the walls of the sampling system or other fluidics required to bring the sample from the eye surface to the sensing electrodes.

As a result, ensuring a consistent reproducible volume of fluid in the electrochemical sensing area (the functionalized electrodes) is extremely difficult without increasing the volume—diluting the target concentration by a known factor which can then be accounted for to calculate the original sample concentration. Furthermore, tears do not contain the high concentrations of redox mediators such as ferrocyanide which are needed for the electrochemistry to work. Thus, it would be difficult for an actual sensor device to avoid diluting the 40 nM or so of cortisol with additional reagents, in order to both increase the total liquid volume to a workable amount that ensures a consistent volume can reach the functionalized electrode area every time, and provide a sufficient mediator concentration for the sensor's electrochemistry. Because of this, a commercially viable tear cortisol sensor must provide reproducible measurements not in the 1-100 nM range, but rather in the range below 10 nM (for example, when a sample with abnormally low cortisol level is diluted even further by the device during processing).

This is precisely what the EIS-based assay presented here allows. With an LLD of below 0.02 nM, a 10 μL tear sample with 40 nM cortisol could be diluted 100× and still be well within the linear range of an EIS-based cortisol sensor. The cortisol assay shown here is therefore more than capable of meeting the technical challenge of distinguishing among low cortisol concentrations in tears.

In this work, the measurement of very low concentrations of cortisol is demonstrated with reproducibility and high sensitivity using a simple and label-free EIS-based biosensor. A replicated sensor set yielded optimal binding at 1.184 Hz with a reproducibility, at highest variability under 10% relative standard deviation. The degree of fit was measured to be 0.9532 with a responsivity of 31.672 ohms/pg/mL and a lower limit of detection of 18.73 pM. This work shows that accurate and quick measurement of small changes in cortisol levels, even those as low as typically found in human tear fluid, is technologically feasible, even after accounting for the practicalities of physical sensor design which may require further dilution of already low-concentration targets for reproducible performance.

Figure 4:
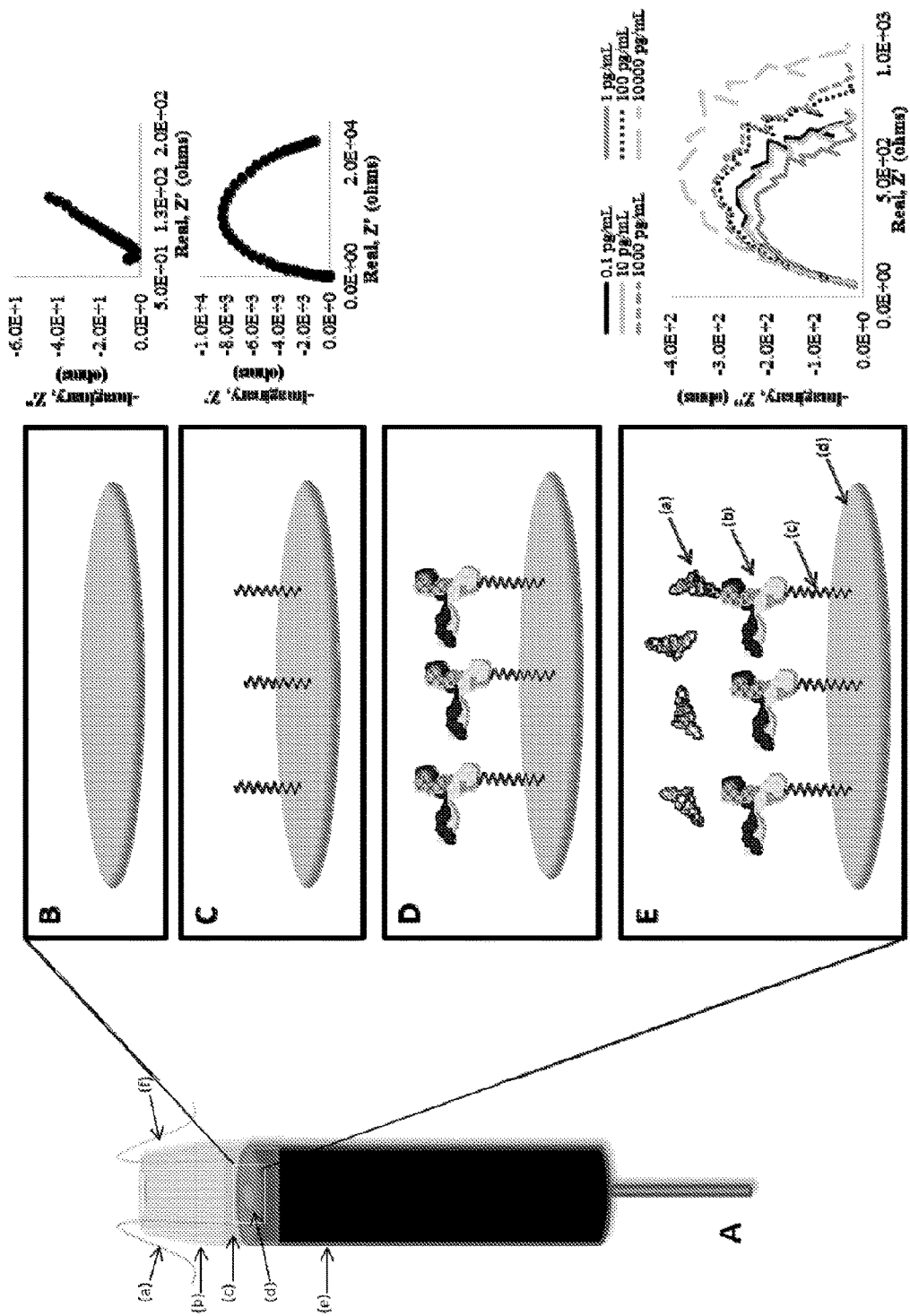
FIG. 4. A. A basic scheme of an embodiment of an apparatus with three-electrode system including (a) Ag/AgCl Reference Electrode, (b) Sensing Well, (c) Sample, (d) Au Working Electrode, (e) GDE, and (f) Pt Counter Electrode. Note that all materials are exemplary and be substituted for by other suitable materials. Additionally, a multiplexible electrochemical impedance spectroscopy (MEIS) system in operable connection with the apparatus is schematically depicted. B. Sample with target (a) Cortisol is placed within the sensing well on surface of covalently immobilized monoclonal antibody (MAb) on the gold working electrode surface with MAb (b) immobilized to the gold surface (d) covalently with 16-MHDA (c) and EDC/NHS. Cortisol (a) target in sample binds to the MAb.
Figure 5A:
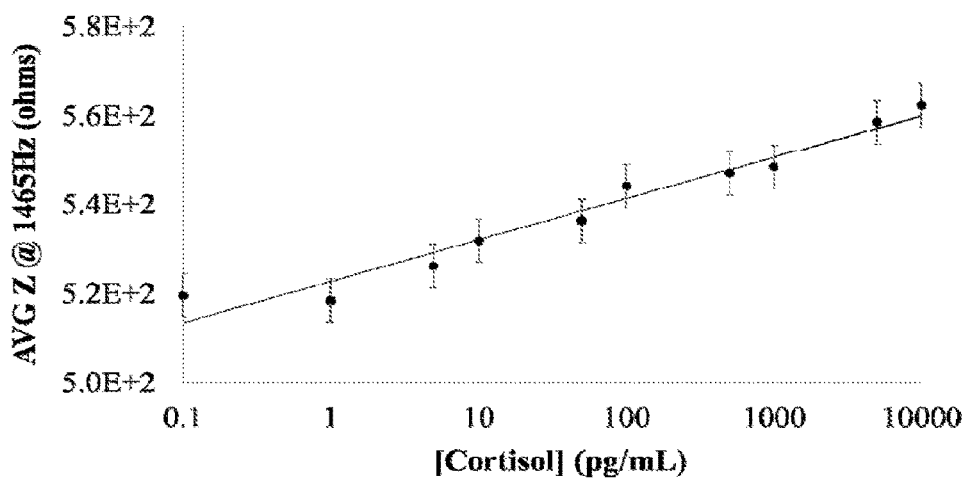
FIGS. 5A-5I. Detection of biomarkers in tear simulated fluid. A calibration curve used in a cortisol device to correlate measured impedance to a concentration of cortisol, as well as plots showing the detection of many different biomolecules by a device of the invention.
Figure 5B:
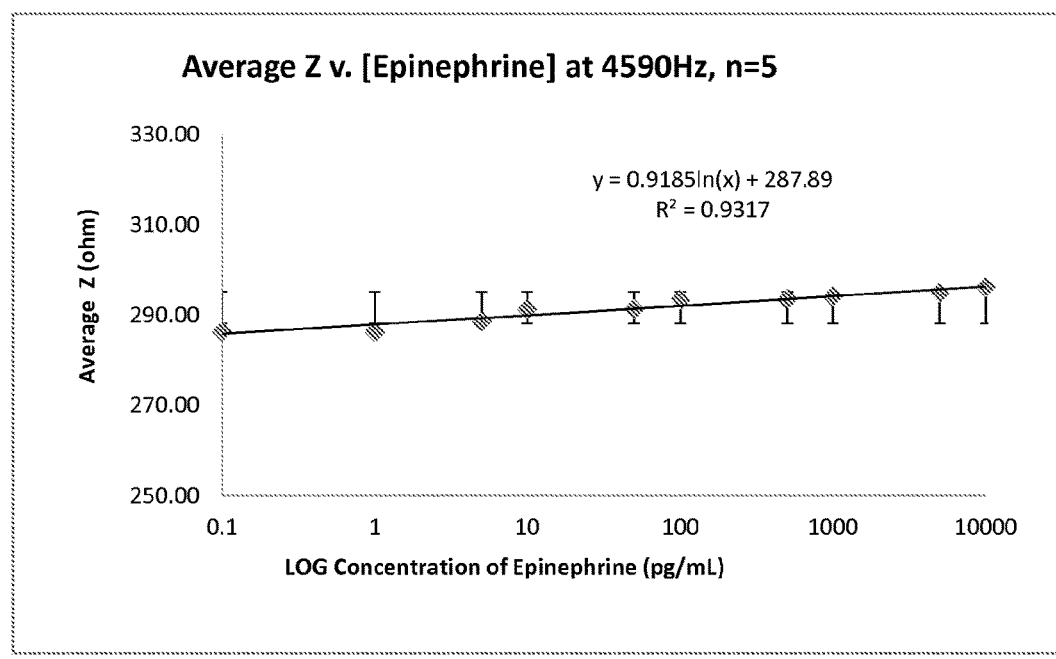
Figure 5C:
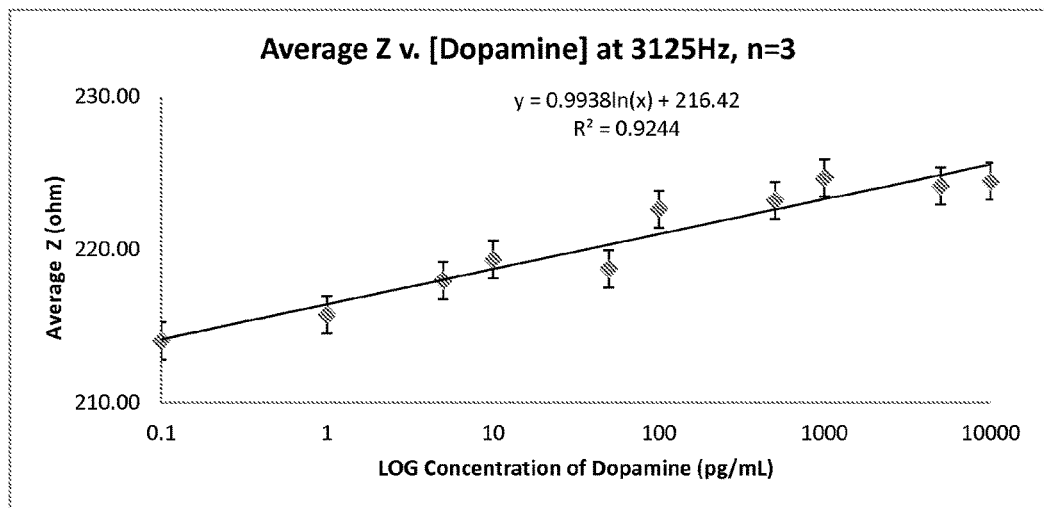
Figure 5D:
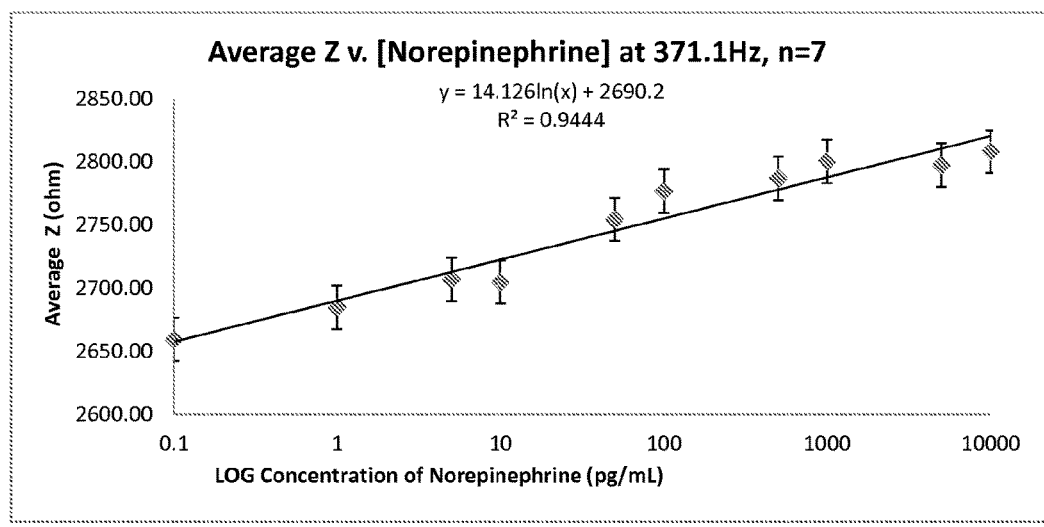
Figure 5E:
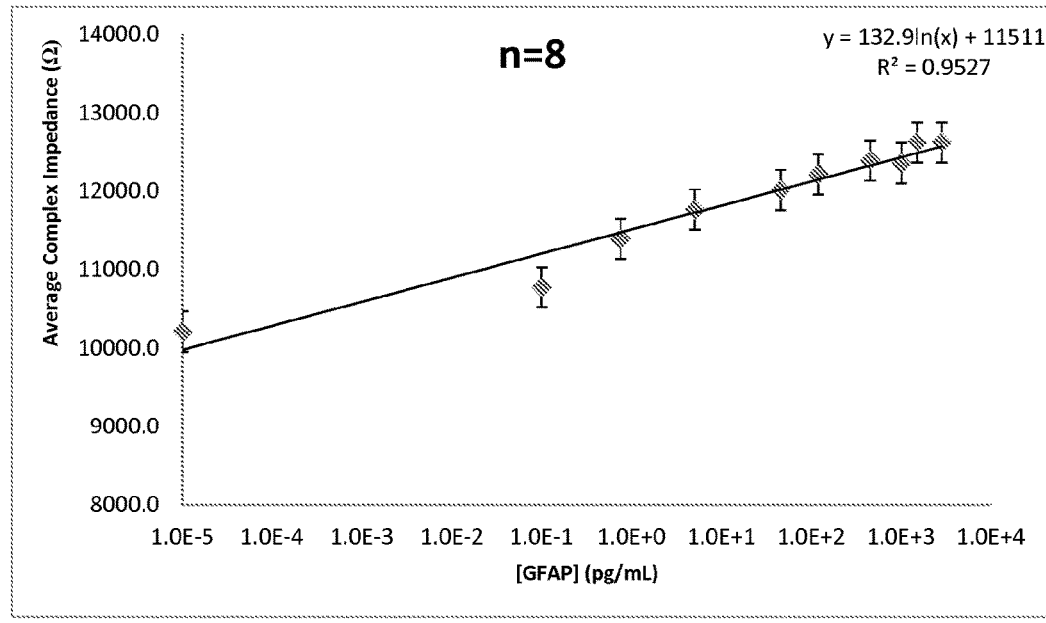
Figure 5F:
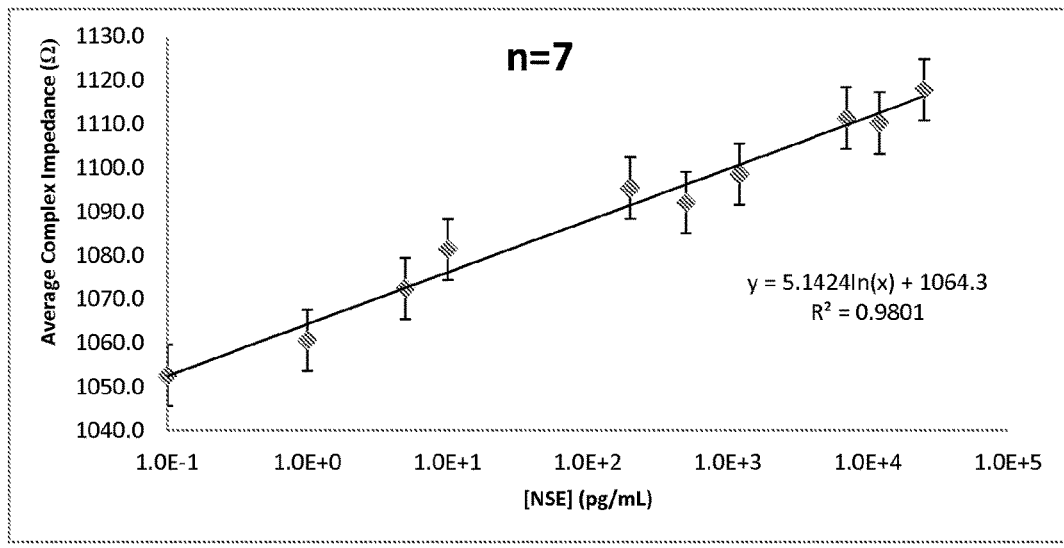
Figure 5G:
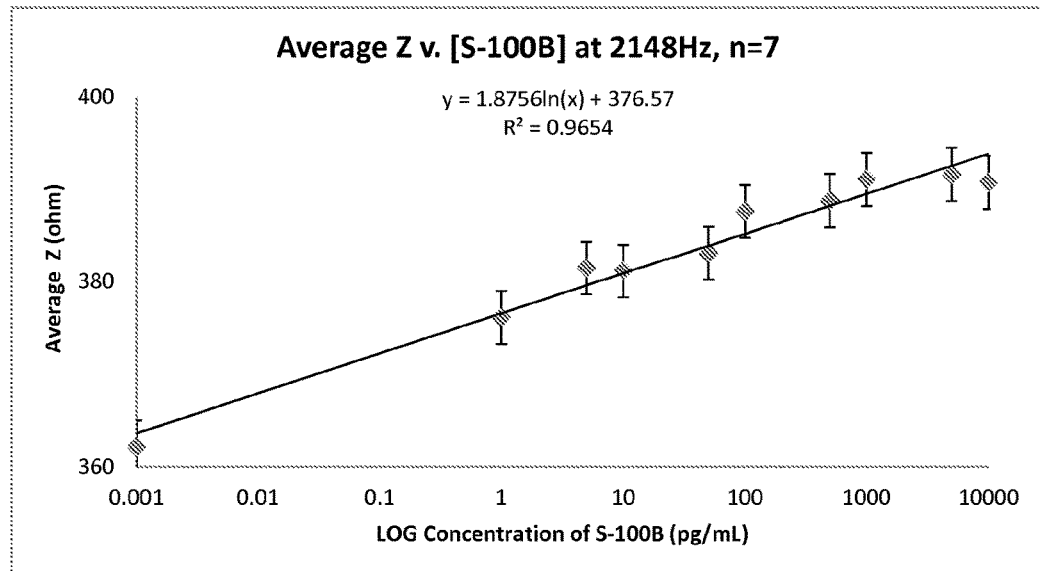
Figure 5H:
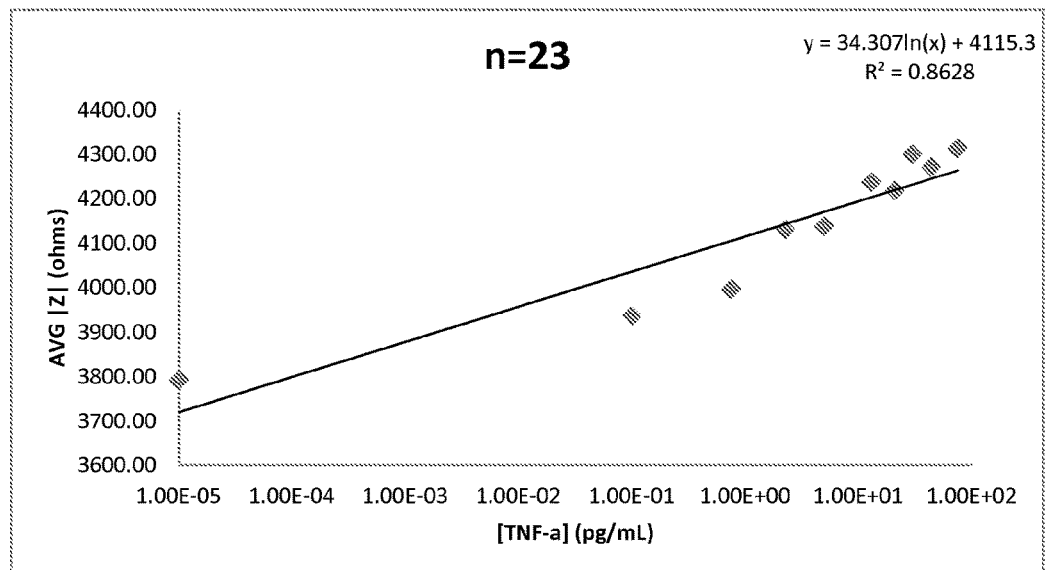
Figure 5I:
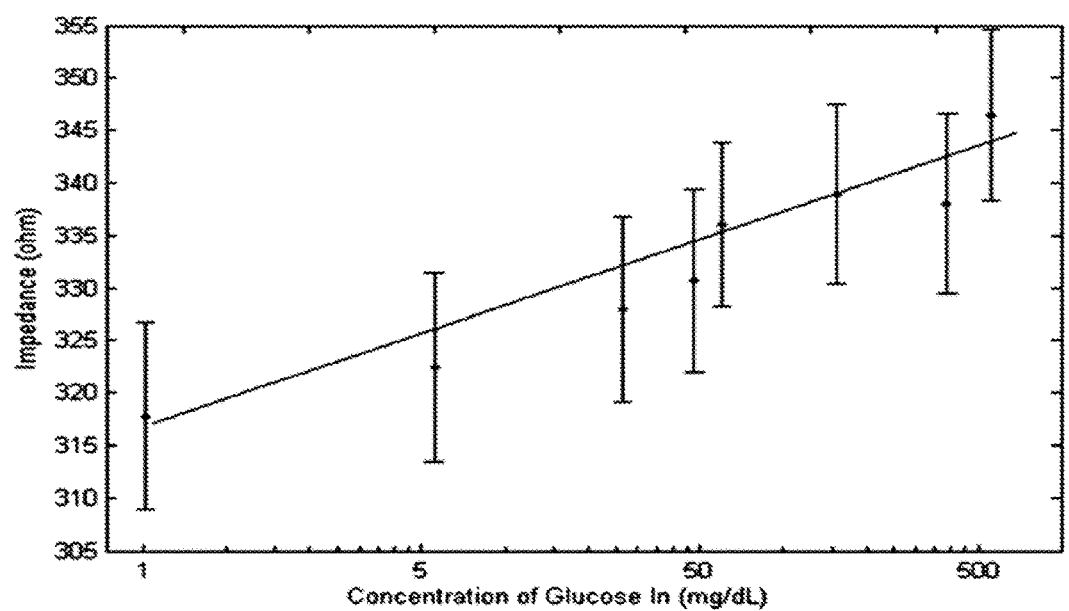
Figure 6A:
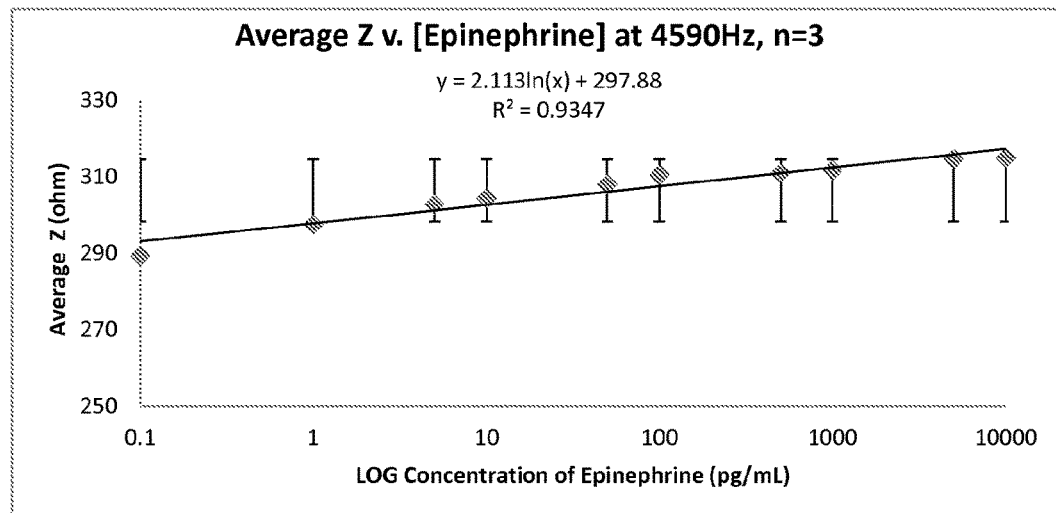
FIGS. 6A-6F show depictions of biomarker detection data in blood.
Figure 6B:
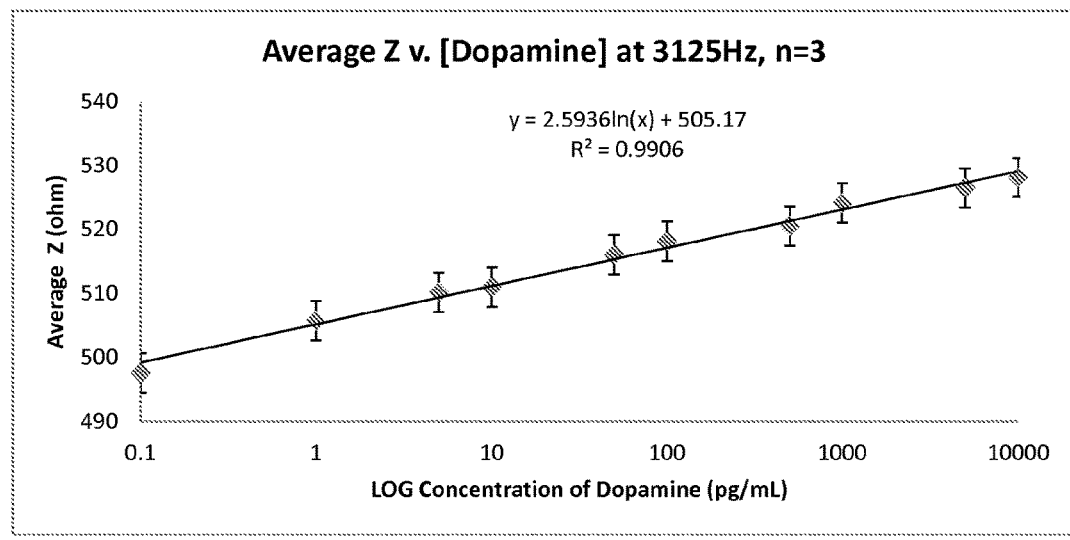
Figure 6C:
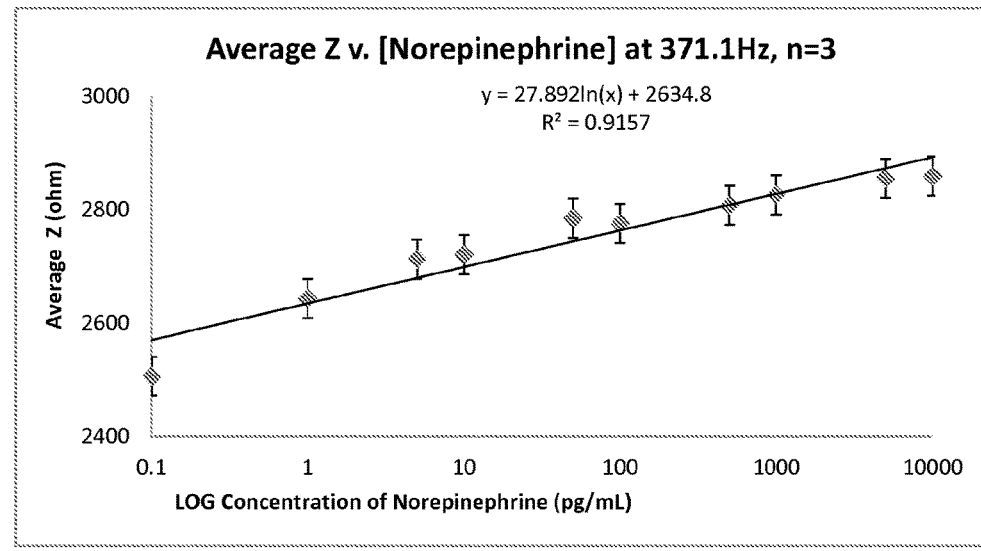
Figure 6D:
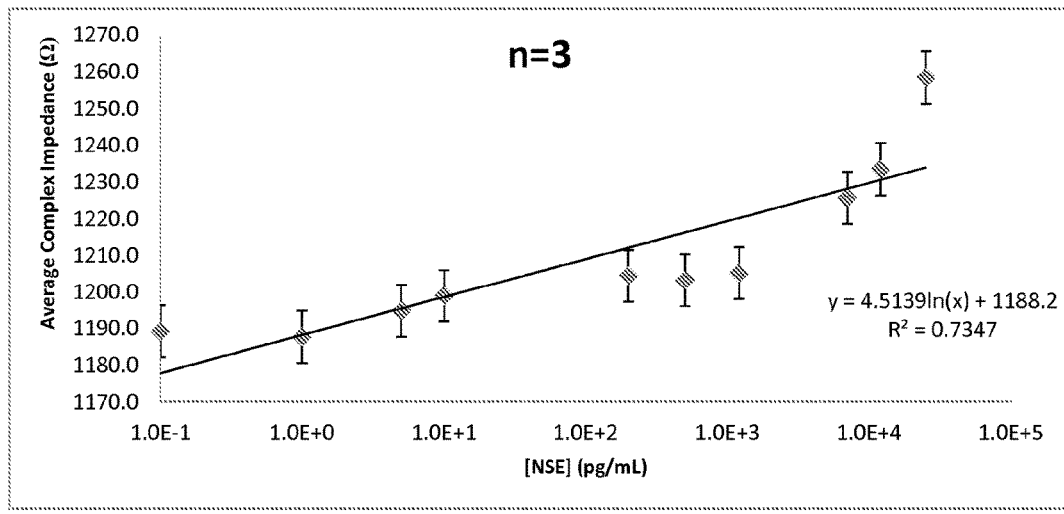
Figure 6E:
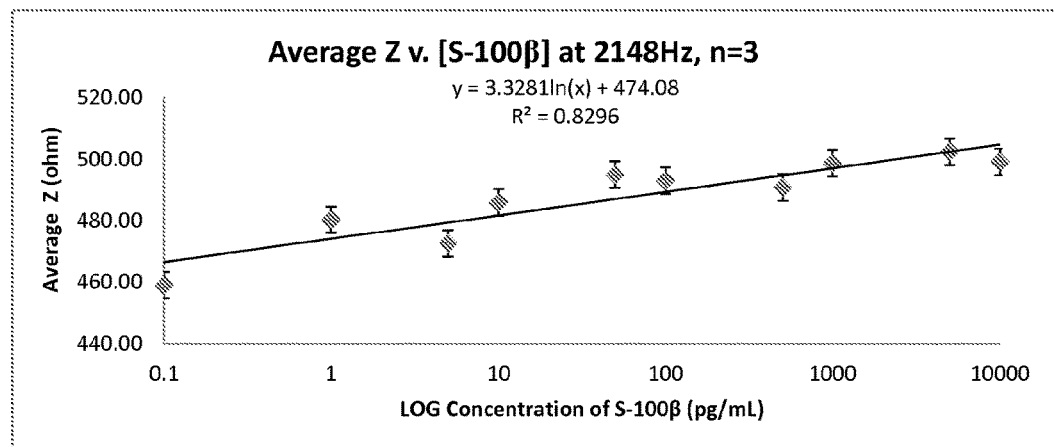
Figure 6F:
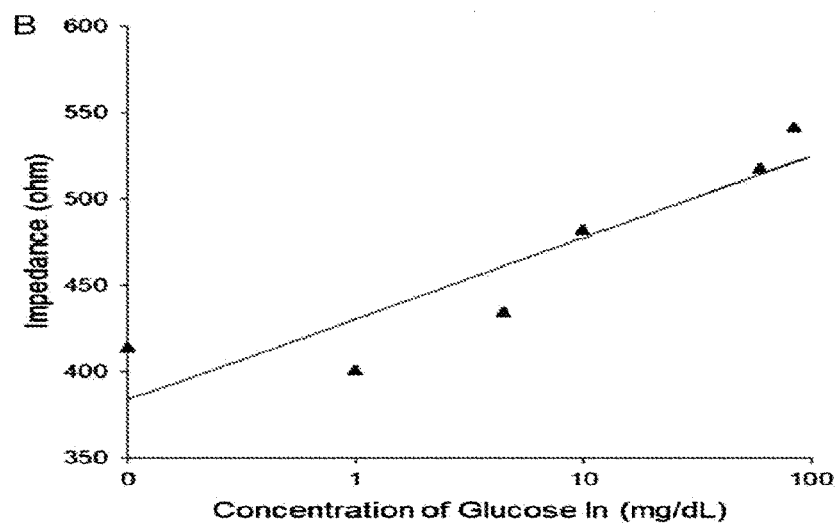
Figure 8:
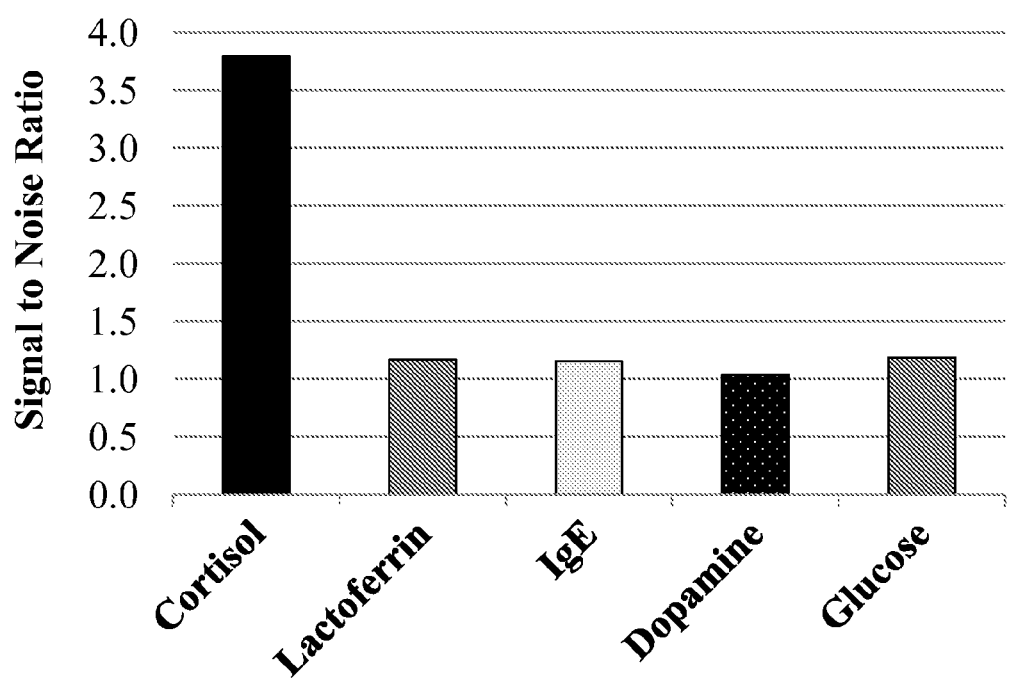
FIG. 8. Cortisol interferents test results. The signal to noise ratio result from an ELISA assay using IgG anticortisol antibody against the provided standard, the usual cortisol gradient, and the tested interferents at 200 pg/mL of each respective analyte is depicted.

In another aspect of the disclosure herein, a screen printed electrode, an embodiment of which is shown in FIG. 4, captures a body fluid sample via a novel microfluidic capture system that brings the sample to the reagents and one or more molecular recognition units for cortisol (or other stress markers found in fluids) encapsulated in the mesoporous carbon inks of the sensor themselves has been developed using rapid, label-free and multiplexible electrochemical impedance spectroscopy (MEIS) that can be utilized at the point on care/injury. While tear fluid is used in this embodiment, blood can also be used as shown in FIG. 6.

The molecular recognition units may include one or more of antibodies, aptamers, peptides, synbodies, nucleic acids, tentacle probes, proteins, and the like. Moreover, mesoporous carbon inks have been found to block interferents, leading to better test results.

EXAMPLE 2

While the following example is for detection of cortisol, similar protocols are used for detection of other biomolecules of interest. Tear fluid or blood are used in this example but other bodily fluids may be used as well.

A standard three-electrode system was used for impedance spectroscopy measurements. The system is comprised of a Ag/AgCl reference electrode (CH Instruments, Austin, Tex.), a gold disk working electrode (GDE) (CH Instruments, Austin, Tex.), and a platinum counter electrode (CH Instruments, Austin, Tex.), with anti-cortisol antibodies (Sigma-Aldrich, St. Louis, Mo.) covalently attached to the working electrode surface to detect cortisol in the sample solution. A 1000 μL pipette tip (VWR International, Radnor, Pa.) was with the tip clipped with a razor and fitted tightly over the GDE to create a plastic "well" able to hold around 0.2 mL of sample liquid. A diagram of this system is shown in FIG. 4.

Phosphate buffered saline (PBS) at pH 7.4 (EMD Biosciences, La Jolla, Calif.) was used to make all solutions unless otherwise noted. In order to immobilize anti-cortisol antibody onto the surface of the gold disk electrode (GDE), the GDE was first wet-polished with 120 figure-eight passes on 3 μm aluminum oxide grit (CH Instruments, Austin, Tex.) and rinsed with distilled water. The 120 figure-eight polishing was then repeated with 1 μm and then 0.05 μm grit (CH Instruments, Austin, Tex.), after which the GDE was sonicated for 20 min in distilled water. Then, 100 μL of a 1 mM 16-mercaptohexadecanoic acid (16-MHDA) (Sigma-Aldrich, St. Louis, Mo.) solution in reagent grade ethanol was placed into the sensing well and sealed in with Parafilm for 1 hr at room temperature. Next, the surface and sides of the GDE and sensing well were carefully rinsed with distilled water. Control EIS measurements were performed on the 16-MHDA-functionalized GDE using a "redox probe" of 100 mM potassium ferrocyanide (Sigma-Aldrich, St. Louis, Mo.) in PBS buffer to ensure an adequate and similar amount of MHDA was immobilized to each GDE. This was determined by analyzing the impedance response of each individual GDE for comparability to one another.

Then, 100 μL of a PBS solution containing 40 mMN-(3-dimethylaminopropyl)-N-ethylcarbodiimide (EDC) (Pierce Biotechnology) and 10 mM N-hydroxysulfosuccinimide (sulfo-NHS) (VWR international) was placed in the sensing well. After 1 hr of incubation at room temperature, the electrode was rinsed with PBS buffer. Next, a 100 μL droplet of a 10 μg/ml solution of anti-cortisol IgG (Aldrich) in PBS buffer was placed on the electrode and left at room temperature for 1 hr, then rinsed off with PBS buffer. Finally, 100 μL of 1 mM ethanolamine (Sigma-Aldrich, St. Louis, Mo.) in distilled water was added to the sensing well and incubated for 30 min at room temperature to block all the unreacted carboxyl groups of the 16-MHDA and EDC/NHS. The electrode was then rinsed carefully with PBS buffer and stored in PBS at 4° C. until use.

Electrochemical impedance measurements were made using a CHI660C Electrochemical Workstation (CH Instruments, Houston, Tex.). Cortisol (Sigma-Aldrich, St. Louis, Mo.) sample concentrations from 0 to 10,000 pg/mL (0 to 27.59 nM) were made in redox probe solution and stored at 4° C. until use. Each concentration of cortisol was then measured on each of the antibody-immobilized electrodes.

For each measurement, 100 μL of the cortisol and redox probe solution was placed in the sensing well of the antibody-immobilized GDE. The AC potential applied to the sample had an amplitude of 5 mV with a formal potential (DC offset) of 150 mV, determined by a CV run on the bare (pre-immobilization) electrodes with redox probe. The AC voltage was applied at a range of frequencies from 1 to 100,000 Hz in 90 sec scan and the impedance magnitude and phase were recorded at each frequency for that sample. Real and imaginary impedances were calculated and plotted in a Nyquist plot for each sample. After each measurement, the GDE and sensing well were rinsed thoroughly with PBS prior to adding the next sample.

For each electrode at each AC frequency tested, the impedance magnitude at each cortisol concentration was correlated to log(concentration) with a slope and $R^2$ calculated. The impedance slopes and $R^2$ values were each plotted against frequency in order to find the frequency which resulted in the best balance of high slope and $R^2$. The impedance values measured at this "optimal" frequency were then used to generate the final concentration gradient allowing cortisol concentration to be estimated from impedance.

As expected, when the concentration of biomarker in vitro and therefore bound to the antibody increased, the impedance measured by the system (and therefore the signal) increased as well. See FIGS. 5A-5I through FIG. 8.

In this work, the measurement of very low concentrations of cortisol is demonstrated with reproducibility and high sensitivity using a simple and label-free EIS-based biosensor. A replicated sensor set yielded optimal binding at 1.184 Hz with a reproducibility, at highest variability under 10% relative standard deviation. The degree of fit was measured to be 0.9532 with a responsivity of 31.672 ohms/pg/mL and a lower limit of detection of 18.73 pM. This work shows that accurate and quick measurement of small changes in cortisol levels, even those as low as typically found in human tear fluid, is technologically feasible, even after accounting for the practicalities of physical sensor design which may require further dilution of already low-concentration targets for reproducible performance.

Moreover, as summarized in FIG. 7, many biomolecules of interest can be detected, such as cortisol, glucose, lactate, lactoferrin, IgE, catecholamines, S-100 beta, neuron specific enolase, glial fibrillary protein, and tumor necrosis factor-alpha.

Figure 9:
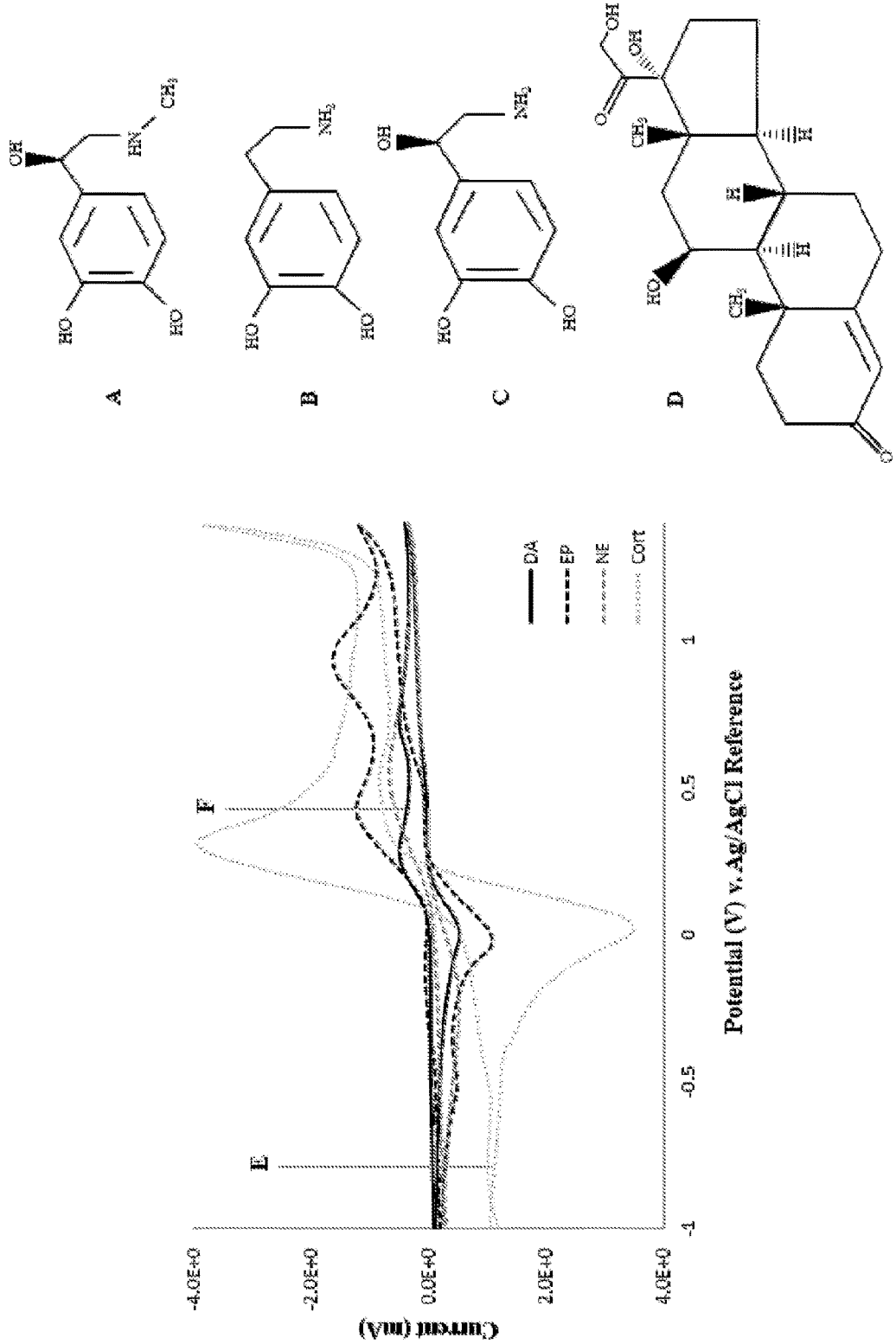
FIG. 9 depicts a summary of stress biomarker data utilizing cyclic voltammetry.
Figure 10:
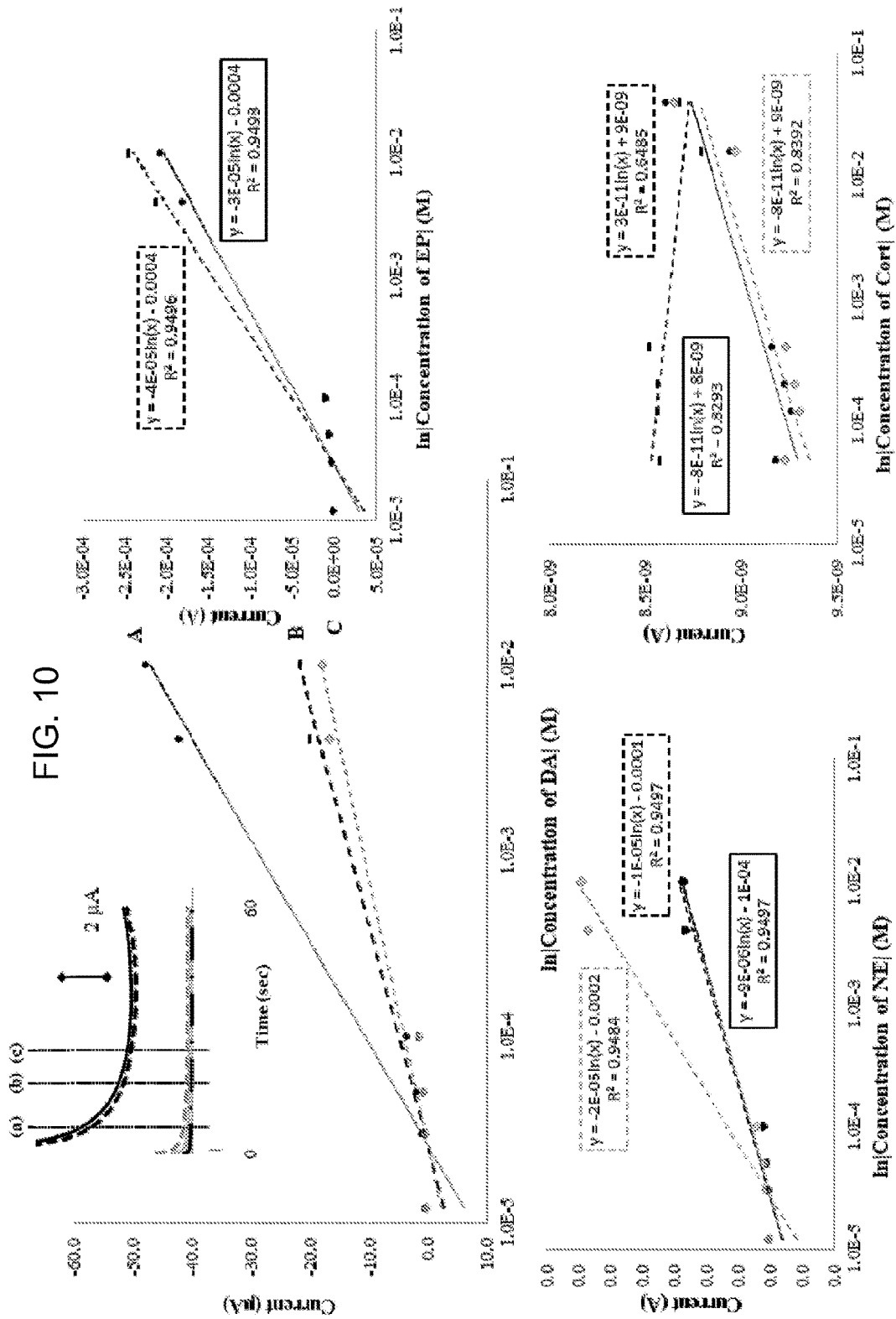
FIG. 10 depicts stress biomarker data using an amperometric technique.
Figure 11:
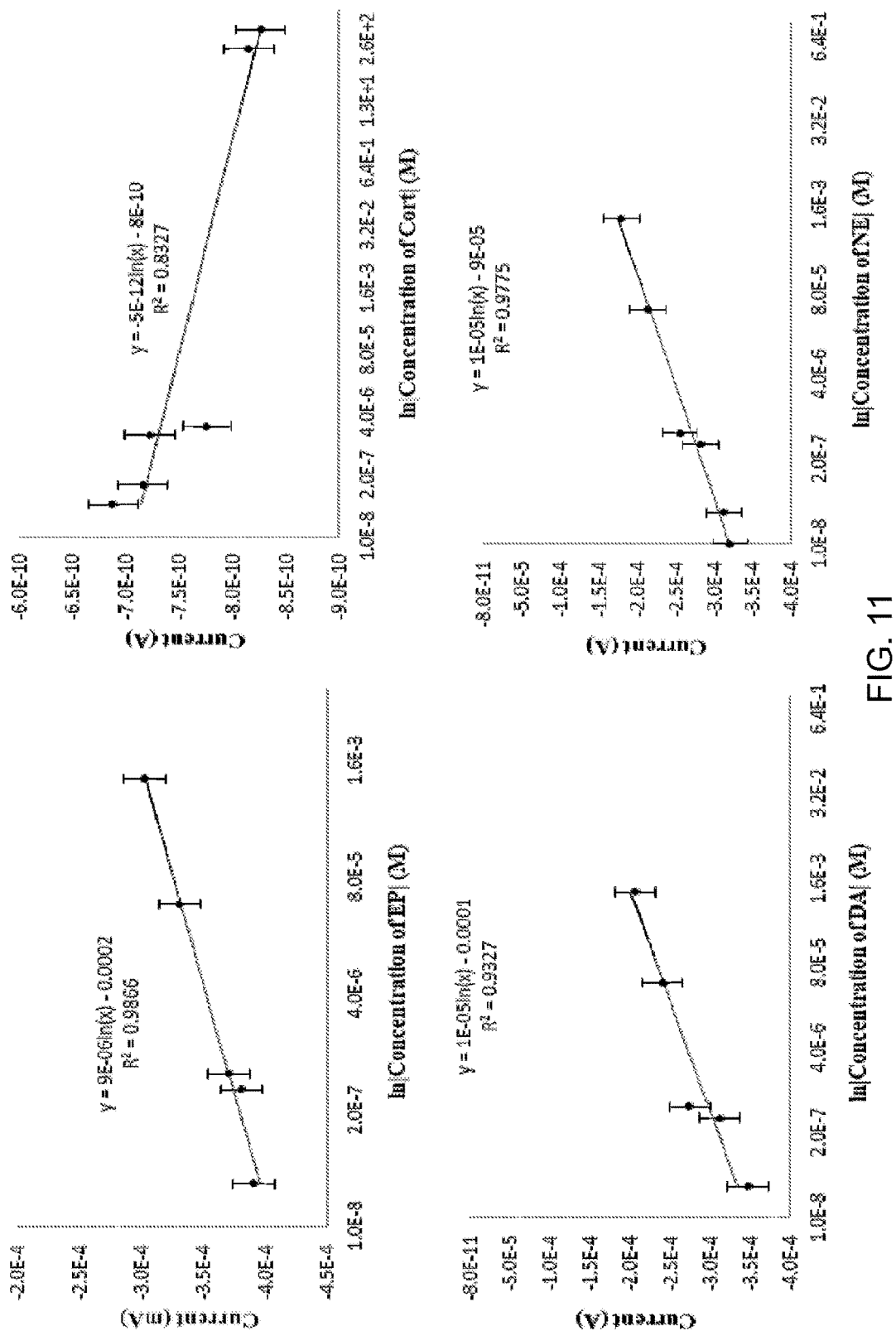
FIG. 11 depicts stress biomarker data using the SWV (Square Wave Voltammetry) technique.

Turning to FIGS. 9-11, a summary of stress biomarker data is depicted. Cyclic Voltammetry (CV) is an electrochemical technique which measures the current that develops in an electrochemical cell under conditions where voltage is in excess of that predicted by the Nernst equation. CV is performed by cycling the potential of a working electrode, and measuring the resulting current. FIG. 9 shows a CV overlay of A EP, B NE, C DA, and D Cort (see structures in figure). Concentrations of DA, EP, Cort, and NE are 0.04M, 0.04M, 0.04M, and 0.1M respectively. Minimal overlapping of signals is indicated by E, where F indicates large overlapping of signal peaks.

FIG. 10 depicts stress biomarker data from an amperometric technique. Amperometry in chemistry and biochemistry is the detection of ions in a solution based on electric current or changes in electric current. (Inlaid) An Amp-it of DA with the voltage applied at the oxidation peak of the CV, 0.52V, at A 2 sec, B 12 sec, C 20 sec during the AMP-it. The outer graph is a calibration curve which plots current versus concentration of DA at times (a), (b), and (c) during the AMP-it. Logarithmic fits of this calibration curve at different times A, B, and C have $R^2$ of 0.9566, 0.9547, and 0.9540 respectively.

FIG. 11 depicts the SWV (Square Wave Voltammetry) technique at 30 Hz used to determine concentration of EP v. current at the oxidation peak, 0.23 V. The SWV technique at 20 Hz is used to determine concentration of DA v. current at the oxidation peak, 0.22 V. The SWV technique at 20 Hz used to determine concentration of NE v. current at the oxidation peak, 0.23 V. The SWV technique at 15 Hz is used to determine concentration of Cort v. current at the oxidation peak, 0.18 V.

The embodiments described above are not intended to be limiting.

What is claimed is:

1. An electrochemical sensor, comprising:
   a reference electrode and a counter electrode;
   a sensing well disposed between said reference electrode and said counter electrode; and
   a functionalized working electrode encapsulated in a mesoporous carbon ink and disposed within said sensing well; wherein
   one or more of a molecular recognition unit to a stress marker is coupled to said functionalized working electrode.

2. The sensor of claim 1, wherein said one or more molecular recognition units comprise monoclonal antibodies are covalently attached to a 16-mercaptohexadecanoic acid functionalized working electrode.

3. The sensor of claim 2, wherein said one or more monoclonal antibodies are attached to said functionalized working electrode with zero-length crosslinkers N-(3-dimethylaminopropyl}-N-ethylcarbodiimide and 1 OmM N-hydroxysulfosuccinimide.

4. The sensor of claim 3, wherein said reference electrode comprises a Ag/AgCl electrode.

5. The sensor of claim 4, wherein said counter electrode comprises a Pt electrode.

6. The sensor of claim 1, further comprising a multiplexible electrochemical impedance spectroscopy system in operable arrangement therewith.

7. The sensor of claim 1, wherein said reference electrode and said counter electrode are disposed both within and outside of said sensing well.

8. The sensor of claim 1, wherein said reference electrode and said counter electrode are disposed along a sidewall within said sensing well.

* * * * *

UNITED STATES PATENT AND TRADEMARK OFFICE
CERTIFICATE OF CORRECTION

PATENT NO. : 10,386,321 B2
APPLICATION NO. : 15/503364
DATED : August 20, 2019
INVENTOR(S) : Jeffrey LaBelle et al.

It is certified that error appears in the above-identified patent and that said Letters Patent is hereby corrected as shown below:

In the Claims

Claim 3, Lines 2 and 3, "1 OmM N-hydroxysulfosuccinimide" should read --1OmM N-hydroxysulfosuccinimide--

Signed and Sealed this
Twenty-ninth Day of October, 2019

Andrei Iancu
*Director of the United States Patent and Trademark Office*